(12) United States Patent
Stewart et al.

(10) Patent No.: US 7,466,146 B2
(45) Date of Patent: Dec. 16, 2008

(54) FROZEN MATERIAL DETECTION USING ELECTRIC FIELD SENSOR

(75) Inventors: Bradley Clayton Stewart, Phoenix, AZ (US); Sergio Garcia de Alba Garcin, Jalisco (MX); Rogelio Reyna Garcia, Jalisco (MX); Gabriel Sanchez Barba, Jalisco (MX); David L. Wilson, Muskego, WI (US)

(73) Assignee: Freescale Semiconductor, Inc., Austin, TX (US)

( * ) Notice: Subject to any disclaimer, the term of this patent is extended or adjusted under 35 U.S.C. 154(b) by 309 days.

(21) Appl. No.: 11/373,071

(22) Filed: Mar. 10, 2006

(65) Prior Publication Data

US 2007/0209446 A1 Sep. 13, 2007

(51) Int. Cl.
*G01R 27/26* (2006.01)
*G01R 29/12* (2006.01)
*F25D 21/02* (2006.01)
*G08B 19/02* (2006.01)
*G08B 21/00* (2006.01)

(52) U.S. Cl. .................. 324/663; 324/671; 324/686; 324/688; 324/457; 62/128; 340/580; 340/962

(58) Field of Classification Search .......... 324/663; 62/128; 340/580, 962
See application file for complete search history.

(56) References Cited

U.S. PATENT DOCUMENTS

| 4,121,433 A | * | 10/1978 | Pomerantz | 340/581 |
| 4,347,709 A | * | 9/1982 | Wu et al. | 340/580 |
| 5,134,380 A | * | 7/1992 | Jonas | 324/663 |
| 5,247,261 A | | 9/1993 | Gershenfeld | |
| 5,569,850 A | * | 10/1996 | Rauckhorst, III | 340/580 |
| 5,761,919 A | * | 6/1998 | Wilson et al. | 62/138 |
| 5,844,415 A | | 12/1998 | Gershenfeld et al. | |
| 5,874,672 A | * | 2/1999 | Gerardi et al. | 324/688 |
| 5,936,412 A | | 8/1999 | Gershenfeld et al. | |

(Continued)

OTHER PUBLICATIONS

Freescale Semiconductor Technical Data; "Electric Field Imaging Device"; Apr. 2005; 22 pp.; Freescale Semiconductor, Inc. http://www.freescale.com/files/analog/doc/data_sheet/MC33794.pdf.

(Continued)

*Primary Examiner*—Timothy J Dole
(74) *Attorney, Agent, or Firm*—Joanna G. Chiu (57) ABSTRACT

An electric field sensor may be used to detect accumulation of frozen material. In one embodiment, an e-field system includes a first electrode, a second electrode located at a distance from the first electrode, the second electrode forming a capacitive element with the first electrode, wherein a gap is present between the first and second electrodes, and an electric field sensor having an electrode terminal coupled to the first electrode and providing an electric field output value representative of an amount of frozen material located in the gap between the first and second electrodes. The system may also include a first insulator adjacent the first electrode and outside the gap, and a conductive layer adjacent the first insulator, where the first insulator is between the first electrode and the conductive layer, and where a shield output of the electric field sensor is coupled to the conductive layer.

18 Claims, 8 Drawing Sheets

U.S. PATENT DOCUMENTS

| | | |
|---|---|---|
| 6,242,714 B1 * | 6/2001 | Narumiya et al. ........... 219/385 |
| 6,335,642 B1 * | 1/2002 | Hiroshima et al. .......... 324/691 |
| 6,601,396 B2 | 8/2003 | Bair, III et al. |
| 6,772,597 B1 | 8/2004 | Zentner et al. |
| 6,794,728 B1 * | 9/2004 | Kithil ......................... 257/532 |
| 6,837,060 B2 | 1/2005 | Collins |
| 6,891,382 B2 | 5/2005 | Post et al. |

OTHER PUBLICATIONS

Stewart, Brad; "Beyond Touch Panels: Appliance Solutions Using Electric Field Sensors"; 56th Annual International Appliance Technical Conference and Exhibition; Mar. 28-30, 2005; 10 pg article & pp. 1 & 4 of Conference Schedule; Rosemont, IL.

Motorola Semiconductor Products Sector; "Maximizing Cost Effectiveness"; Mar. 2004; Accompanying Declaration.

* cited by examiner

FROZEN MATERIAL DETECTION USING ELECTRIC FIELD SENSOR

FIELD OF THE INVENTION

The present invention relates generally to frozen material detection, and more specifically, to frozen material detection using an electric field sensor.

RELATED ART

Figure 1:
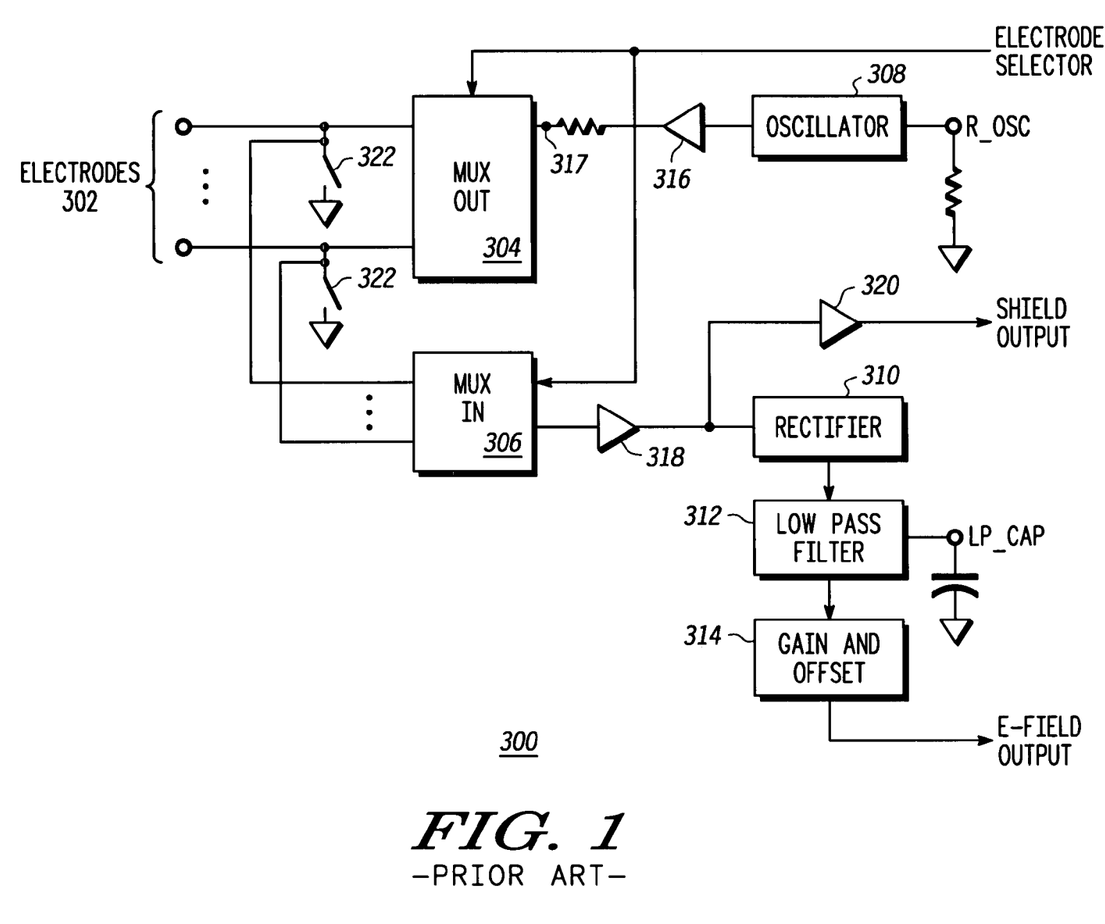
FIG. 1 illustrates, in block diagram form, an e-field sensor currently available.

An electric field (e-field) is a force vector (magnitude and direction) that is present in any region anywhere a charged object experiences an electrostatic force by other charged objects. Many objects can be sensed by their effect on the e-field. FIG. 1 illustrates a basic block diagram of an e-field sensor 300 that may be used to detect an e-field. E-field sensor includes an oscillator 308 coupled via a buffer 316 and a resistor to a multiplexer (MUX) 304. MUX 304 provides N electrode terminals 302. Each of the electrode terminals 302 are also coupled as inputs to a MUX 306 and are also each coupled via a switch 322 to ground. The output of MUX 306 is coupled via a buffer 318 to a rectifier 310. The output of rectifier 310 is coupled to a low pass filter 312, which is coupled to a gain and offset unit 314, which outputs an e-field output. The output of buffer 318 is also provided, via buffer 320, a shield output. The frequency of oscillator 308 can be set by a resistor R_OSC, and low pass filter 312 can be tuned by a capacitor LP_CAP. Each of MUX 304 and 306 also receives an electrode selector which selects one of the N electrode terminals 302.

E-field sensor 300 measures the change in amplitude of an alternating-current (AC) signal in response to the external capacitive load applied to the field. For example, based on the electrode selector, one of the N electrode terminals is coupled to node 317. An external capacitive load coupled to the selected electrode terminal affects the AC signal at node 317. For example, as the external capacitance load increases, the AC signal at node 317 is reduced. Based on the electrode selector, the selected electrode terminal is also coupled to rectifier 310, via MUX 306 and buffer 318. Therefore, the AC signal at node 317 is provided, via MUXes 304 and 306 and buffer 318 to rectifier 310. Rectifier 310 rectifies the signal, low pass filter 312 filters the signal, and gain and offset unit 314 applies any gain or offset, if needed, and outputs the e-field output. The e-field output is therefore proportional to the change in the e-field capacitance of the selected electrode. In one embodiment, e-field output is a voltage between 0 and 5 volts, depending on the e-field capacitance of the selected electrode. An existing e-field sensor available today is the MC33794 E-field sensor integrated circuit available from Freescale Semiconductor, Inc.

BRIEF DESCRIPTION OF THE DRAWINGS

The present invention is illustrated by way of example and not limited by the accompanying figures, in which like references indicate similar elements, and in which.

Skilled artisans appreciate that elements in the figures are illustrated for simplicity and clarity and have not necessarily been drawn to scale. For example, the dimensions of some of the elements in the figures may be exaggerated relative to other elements to help improve the understanding of the embodiments of the present invention.

DETAILED DESCRIPTION OF THE DRAWINGS

As described above, an electric field (e-field) is a force vector (magnitude and direction) that is present in any region anywhere a charged object experiences an electrostatic force by other charged objects. Almost any object that affects the permittivity of a gap between electrodes can be sensed by its effect on the e-field. For example, as will be described in more detail below, the presence of frozen material can be determined by observing the change in dielectric constant, which can be represented by an e-field output of an e-field sensor like the sensor in FIG. 1.

E-field detection functions using the concept that the object that is being detected affects the capacitance of a capacitive element formed by an electrode and some virtual ground (where virtual ground can be an actual or physical ground or can be any point in space that has a different electric charge from the electrode, including the object that is being detected). The formation of this capacitive element causes current to flow from the electrode coupled to the electrode terminal of the e-field sensor through this capacitive element. As the capacitance of the capacitive element increases, the AC current in the e-field sensor (such as, for example, at node 317) increases, the voltage decreases, and the e-field output is proportional to this change in voltage. In one embodiment, an output of 5 Volts corresponds to basically no capacitance formed by the electrode coupled to the electrode terminal of the e-field sensor, with the output decreasing from 5 Volts to 0 Volts as the capacitance detected by the electrode increases.

Note that the capacitance C of a capacitor or capacitive element can be generally expressed as follows:

$$C = \frac{k \varepsilon_0 A}{d}$$

In the above equation, A is the area of the two capacitor electrodes, d is the distance between the electrodes, k is the dielectric constant of the material between the electrodes, and $\varepsilon_0$ is the permittivity of free space. Therefore, note that as distance d decreases, capacitance increases. Therefore, as an object approaches the electrode coupled to an electrode terminal of the e-field sensor, the capacitance is increased, and the e-field output can be used to reflect how close an object is, since the e-field output is inversely proportional to the distance d between the electrode and the approaching object. Also, note that when k increases or decreases (with d and A substantially fixed), the capacitance also increases or decreases, respectively. Therefore, the e-field output of an e-field sensor can also be used to reflect change in the dielectric constant of a capacitor coupled to an electrode terminal of the sensor. For example, the presence of a material such as water or ice can affect the dielectric constant k. Therefore, as will be described in more detail below, the formation of a frozen material between electrodes of a capacitive element coupled to the e-field sensor can be detected by the e-field sensor output which is proportional to the change in capacitance caused by the change in dielectric constant between the electrodes.

Figure 2:
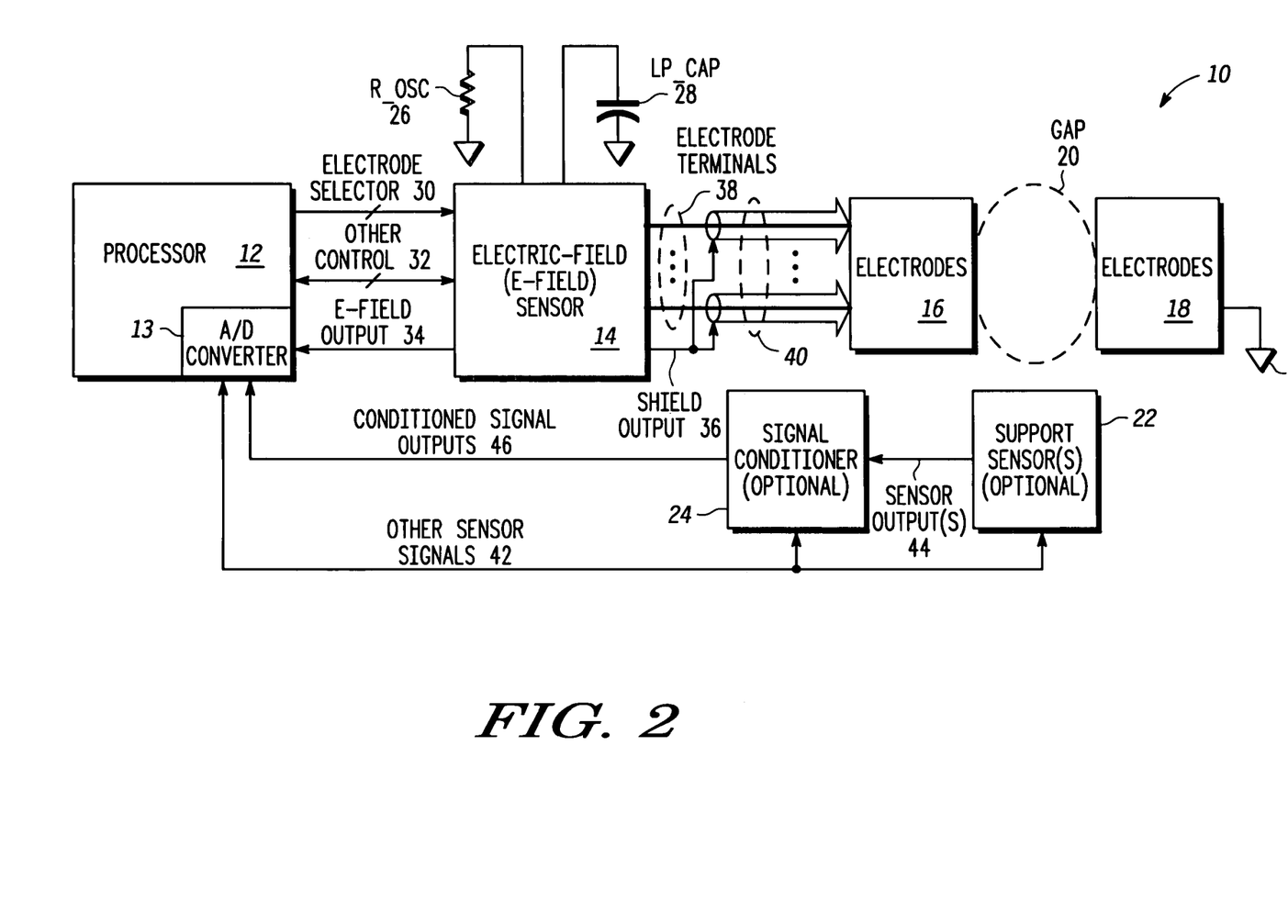
FIG. 2 illustrates, in block diagram form, a e-field sensor system, in accordance with one embodiment of the present invention.

FIG. 2 illustrates an e-field system 10 in accordance with one embodiment of the present invention. System 10 includes a processor 12, an electric field (e-field) sensor 14, electrodes 16, electrodes 18, gap 20, signal conditioner 24, and support sensor(s) 22. Processor 12 provides electrode selector 30 to e-field sensor 14, receives e-field output 34 from e-field sensor 14, and can communicate with e-field sensor via other control signals 32, as needed. Processor 12 also provides other sensor signals 42 to signal conditioner 24 and support sensor(s) 22. Processor 12 can be any type of processor, such as a microcontroller, digital signal processor, etc. Processor 12 also includes an analog to digital (A/D) converter 13 to process e-field output 34 and conditioned signal outputs 46 from signal conditioner 24 as needed for use by processor 12. (In an alternate embodiment, A/D converter 13 may be located external to processor 12. In yet another embodiment, processor 12 may not be present where other processing circuitry may receive and provide the illustrated signals.) Note that an e-field sensor such as e-field sensor 300 described in FIG. 1 can be used for e-field sensor 14. Therefore, the description of FIG. 2 will be provided assuming an e-field sensor like e-field sensor 300 is used as e-field sensor 14.

A resistor, R_OSC 26, is coupled to an oscillator of e-field sensor 14 (such as oscillator 308 of FIG. 1). R_OSC 26 may be used to select the frequency of the oscillator. In one embodiment, R_OSC 26 may be a 39 kilo-ohm resistor. A capacitor, LP_CAP 28, is coupled to a low pass filter of e-field sensor 14 (such as low pass filter 312 of FIG. 1) which may be used to tune the low pass filter. In one embodiment, LP_CAP may be a 10 nano-Farad capacitor. Each of R_OSC 26 and LP_CAP 28 are coupled to ground. E-field sensor 14 also provides N electrode terminals 38, where N can be any integer value greater than or equal to one. E-field sensor 14 also provides a shield output 36. Electrode terminals 38 and shield output 36 are provided to electrodes 16 via N connectors 40, where each electrode terminal corresponds to one connector. In one embodiment, connectors 40 are coaxial cables with a center conductor of each coaxial cable coupled to an electrode terminal and an outer shield of each coaxial cable coupled to shield output 36. Electrodes 16, which are coupled to e-field sensor 14 via connectors 40 will be described in more detail below. Electrodes 18 are coupled to ground 48 and are spaced at a distance from electrodes 16, thus forming a gap 20 between electrodes 16 and electrodes 18. (Note that ground 48 can be a virtual ground or an actual or physical ground.) In one embodiment, electrodes 16 include one electrode corresponding to each electrode terminal of the electrode terminals 38. However, in an alternate embodiment, electrodes 16 may include less than N electrodes. Electrodes 18 can include one or more electrodes. In one embodiment, electrodes 18 include one electrode for each of electrodes 16. Alternatively, electrodes 18 may include fewer or more electrodes.

Support sensor(s) 22 provides sensor output(s) 44 to signal conditioner 24. Support sensor(s) 22 may include one or more support sensors. For example, in one embodiment, support sensor(s) 22 includes a temperature sensor such as a thermistor or a thermocouple to sense temperature and provide temperature information back to processor 12, via signal conditioner 24. In one embodiment, signal conditioner 24 is not present and the output of support sensor(s) 22 can be provided directly to processor 12.

In operation, e-field sensor 14 is used to detect changes in the dielectric constant of gap 20 where e-field output 34 is provided proportional to these changes in dielectric constant. For example, note that electrodes 18 form a capacitive element or capacitive elements with electrodes 16, with the capacitance changing as the dielectric constant of gap 20 changes (assuming that the electrodes are substantially fixed such that the distance between electrodes 16 and 18 does not substantially change). Therefore, as frozen material accumulates between electrodes 16 and electrodes 18, the value of e-field output 34 changes accordingly. For example, the dielectric constant of air is about 1, the dielectric constant of ice is about 5, and the dielectric constant of snow or frost is about 3.2. Therefore, if gap 20 is filled with air, then the capacitance of the capacitive element formed by electrodes 16 and electrodes 18 is less than if gap 20 included ice, snow, or frost. Therefore, as ice, snow, or frost accumulates in gap 20, e-field output 34 decreases.

In one embodiment, the frozen material which accumulates in gap 20 may correspond to frost accumulating on a cooling element (e.g. cooling coil) of a refrigerator or air conditioner. In this embodiment, electrodes 18 may correspond to the cooling element itself. In another embodiment, the frozen material which accumulates in gap 20 may correspond to frost accumulating on a windshield of a transportation device such as an automobile, air craft, or other vehicle. Therefore, using empirical data, a particular value of e-field output 34 can be set as a threshold for indicating that too much frost has accumulated in gap 20 (e.g. on the cooling element or windshield). In other embodiments, accumulation of any material can be detected in gap 20, by determining how the accumulation of material changes the dielectric constant of the capacitive element.

Figure 3:
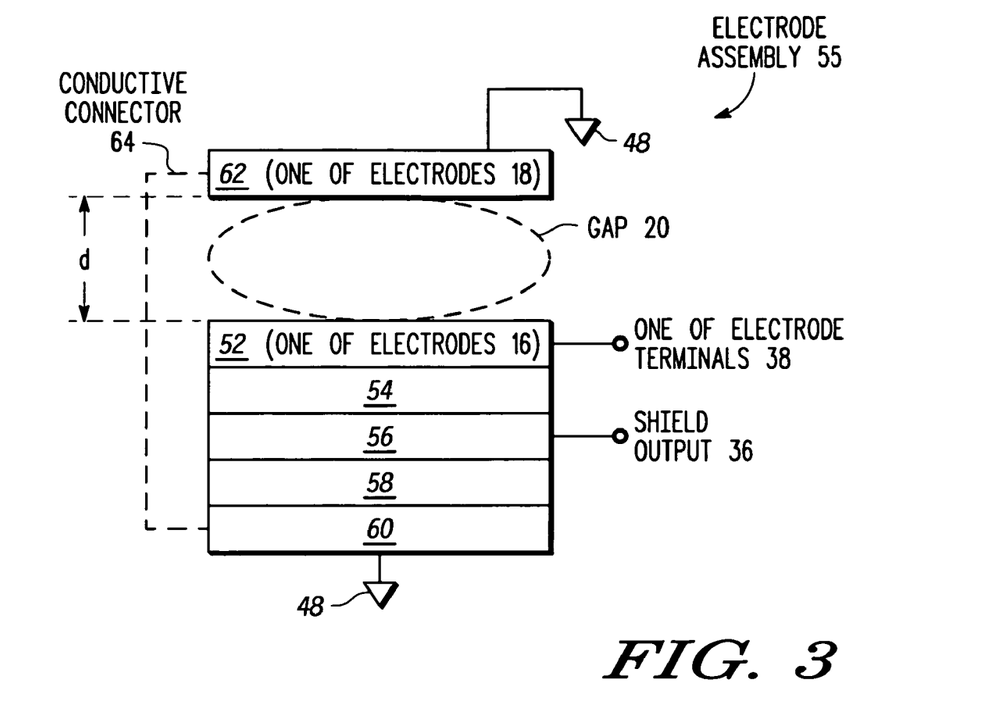
FIGS. 3 and 4 illustrate cross-sectional views of an electrode of the e-field system of FIG. 2, in accordance with embodiments of the present invention.

FIG. 3 illustrates one example of a cross section of a structure of an electrode assembly 55 formed by one of electrodes 16 and electrodes 18, in accordance with one embodiment of the present invention. Electrode assembly 55 includes an electrode 52, corresponding to one of electrodes 16, and an electrode 62, corresponding to one of electrodes 18, spaced apart by a distance, d, to form gap 20. Electrode 52 is coupled to one of electrode terminals 38 via one of connectors 40. Electrode assembly 55 also includes an insulating layer 54 adjacent electrode 52, outside gap 20. For example, in the illustrated embodiment, electrode 52 is located between insulating layer 54 and gap 20. Insulating layer 54 can also be located adjacent sidewalls of electrode 52. In one embodiment, insulating layer 54 is a low-k material having a dielectric constant of less than 10, or, more preferably, less than 7, or even more preferably, less than 5. Electrode assembly 55 also includes a conductive layer 56 adjacent insulating layer 54, where insulating layer 54 is located between conductive layer 56 and electrode 52. Conductive layer 56 is coupled to shield output 36 of e-field sensor 14. This allows the capacitor formed by electrode 52 and electrode 62 to be shielded from other virtual ground sources.

As can be seen in reference to e-field sensor 300 of FIG. 1, shield output 36 and an output at the selected one of electrode terminals 38 are essentially the same signal. That is, the primary difference is that shield output 36 is buffered (e.g. has more output drive), such as via buffers 318 and 320, so that at any instant, there is a very small (approximately zero) net voltage difference between the selected electrode terminal and shield output. Therefore, there is an approximately zero net voltage between electrode 52 and conductive layer 56. Furthermore, as described above, connectors 40 may be implemented with coaxial cables. In this manner, there is approximately zero net voltage between the center conductor (which would be coupled to electrode 52 of FIG. 3) and the outer shield of the coaxial cable (which would be coupled to conductive layer 56) along the length of the coaxial cable.

The illustrated embodiment of FIG. 3 also includes an insulating layer 58 adjacent conductive layer 56 and a conductive layer 60 adjacent insulating layer 58 and coupled to ground 48. Conductive layer 60 may represent nearby conductive surfaces which are typically grounded and that can negatively affect measurements by e-field sensor 14. For example, in one embodiment, conductive layer 60 may be part of a surrounding metal chassis. However, note that by coupling shield output 36 to conductive layer 56, electrode 52 is shielded from the nearby conductive surfaces. Note that without the shielding provided by conductive layer 56 and shield output 36, conductive layer 60 could overpower electrode 52, thus preventing accurate measurements by e-field sensor 14.

In one embodiment, insulating layer 58 is also a low-k material, like insulating layer 54. Therefore, in one embodiment, a same material may be used for insulating layers 54 and 58. Also, in one embodiment, note that conductive layer 60 and electrode 62 can be electrically connected via conductive connector 64.

Figure 4:
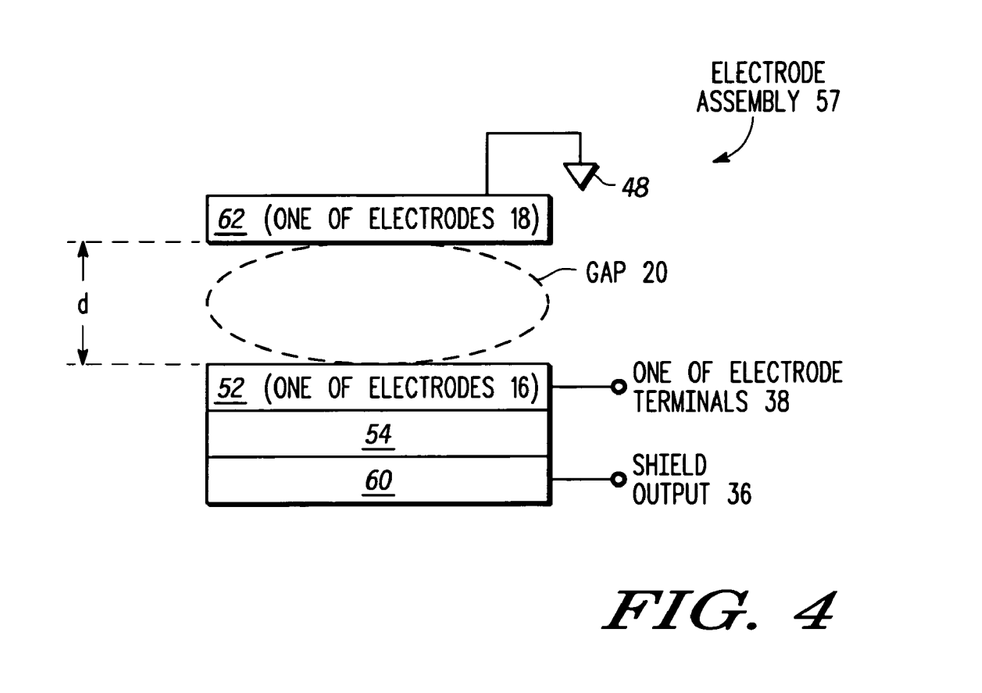

FIG. 4 illustrates an electrode assembly 57 that is an alternate embodiment of electrode assembly 55. Note that electrode assembly 57 does not include conductive layer 56 and does not include insulating layer 58. In this embodiment, a nearby conductive surface (represented by conductive layer 60), such as, for example, a metal chassis can be used as a shield if it is not grounded. In this case, shield output 36 is coupled to conductive layer 60.

Therefore, in either of FIGS. 3 and 4, as frost or any frozen material accumulates in gap 20, the dielectric constant of the capacitor formed by electrodes 52 and 62 changes, resulting in proportional changes in e-field output 34, thus allowing processor 12 (or any other processing circuitry) detect unacceptable levels of frost or frozen material. Alternatively, desired levels of frost or frozen materials can also be detected. Also note that in one embodiment, an electrode assembly may include only electrodes 52 and 62, or may include other layers in addition to or in place of those illustrated in FIGS. 3 and 4, or may include fewer layers.

Figure 5:
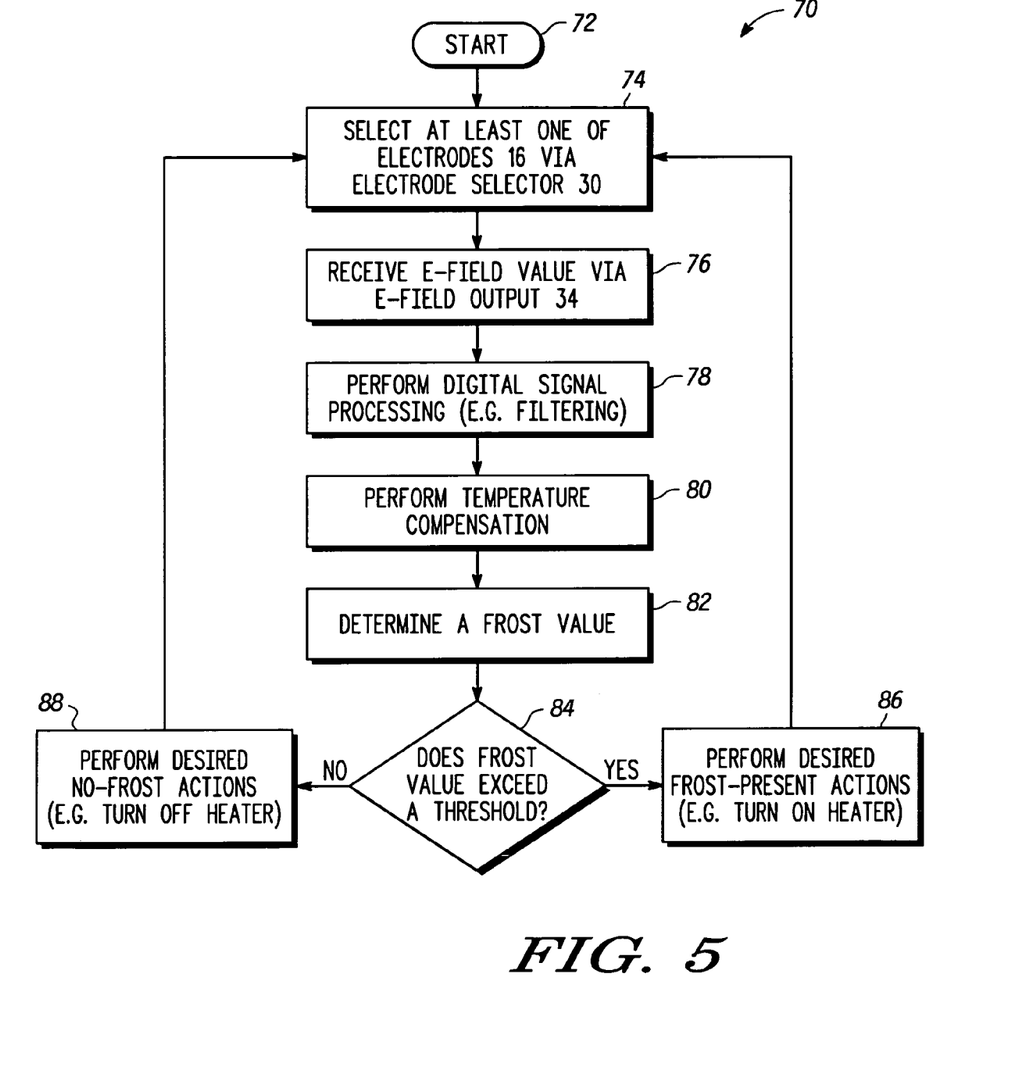
FIG. 5 illustrates a flow diagram performed by the e-field system in FIG. 2 in accordance with one embodiment of the present invention.

FIG. 5 illustrates a flow 70 for frost or frozen material detection performed by system 10 in accordance with one embodiment of the present invention. Flow 70 begins with start 72 and proceeds to block 74 where at least one of electrodes 16 is selected via electrode selector 30. For example, in the case where e-field sensor has 8 electrode terminals, electrode selector 30 may be a 3 bit value to select one of the 8 electrodes. (Therefore, note that electrode selector 30 may use $\log_2 N$ bits to select one of N electrode terminals 38.) This value may be provided by processor 12. As seen in reference to FIG. 1, this value is used by e-field sensor 14 to select an electrode terminal (via MUxes 304 and 306), and therefore, the electrode of electrodes 16 coupled to the selected electrode terminal is used to provide e-field output 34. (Note that in one embodiment, the non-selected electrode terminals are grounded via switches 322.) Flow then proceeds to block 76 where processor 12 receives an e-field value via e-field output 34 which is representative of an amount of frozen material located in gap 20. Flow proceeds to block 78 where digital signal processing, such as filtering, may be performed. Flow then proceeds to block 80 where temperature compensation may also be performed. For example, in one embodiment, a temperature sensor may be used near gap 20 to provide support information to processor 12. For example, based on a detected change in temperature, the e-field value may be compensated accordingly. In alternate embodiments, other types of support sensors may be used in addition to or in place of a temperature sensing. Also, note that blocks 78 and 82 are optional.

Flow then proceeds to block 82, where, as a result of blocks 78 and 80 (if present), a frost value is determined. If blocks 78 and 80 are not present, the frost value may simply correspond to the e-field value (which may have been processed by an A/D converter such as A/D converter 13). Also, note that the frost value may not just correspond to frost, but to any frozen material. Flow then proceeds to decision diamond 84 where it is determined if the frost value exceeds a threshold. For example, using empirical data, a threshold value can be selected such that a frost value which exceeds that threshold indicates a problematic level of frost (or other frozen material) accumulation in gap 20 that has to be addressed. For example, if the frost value does exceed the threshold, flow proceeds to block 86 where desired frost-present actions are taken. For example, a heater may be turned on to melt the frost or other frozen material. Similarly, other actions may be taken to address the frost accumulation to ensure that it falls below the threshold level again (or below another appropriate value which can be selected to allow for appropriate hysteresis).

If, at decision diamond 84, the frost value does not exceed the threshold value, flow proceeds to block 88 where any desired no-frost actions are taken. For example, this may include doing nothing, or may include undoing previous frost-present actions that were performed to reduce frost. Therefore, a no-frost action may include turning off the heater or undoing any other actions which may have been done in block 86. Therefore, note that desired frost-present actions used to reduce the amount of frost accumulation or frozen material accumulation is done only as needed, thus allowing for the conservation of power, money, and other resources. Also, the threshold may be a user programmable value such that different thresholds can be set for different systems having different needs or requirements.

Note that flow 70 of FIG. 5 can be performed for one or more of electrodes 16. For example, in one embodiment, processor 12 can select each electrode terminal of electrode terminals 38, in turn, that is coupled to an electrode of electrodes 16 to detect accumulation of frozen material at different locations and at different points in time. Also, note that a flow similar to flow 70 of FIG. 5 can also be used to detect desired levels of frost or frozen material accumulation rather than problematic levels of accumulations. In this embodiment, different actions may be taken based upon whether the desired level of accumulation has or has not been reached. Furthermore, flow 70 can be implemented in hardware, software, firmware, or in any combination thereof.

FIGS. 6-11 illustrate various configurations of electrodes in reference to a member subject to frozen material accumulation according to various embodiments of the present invention.

Figure 6:
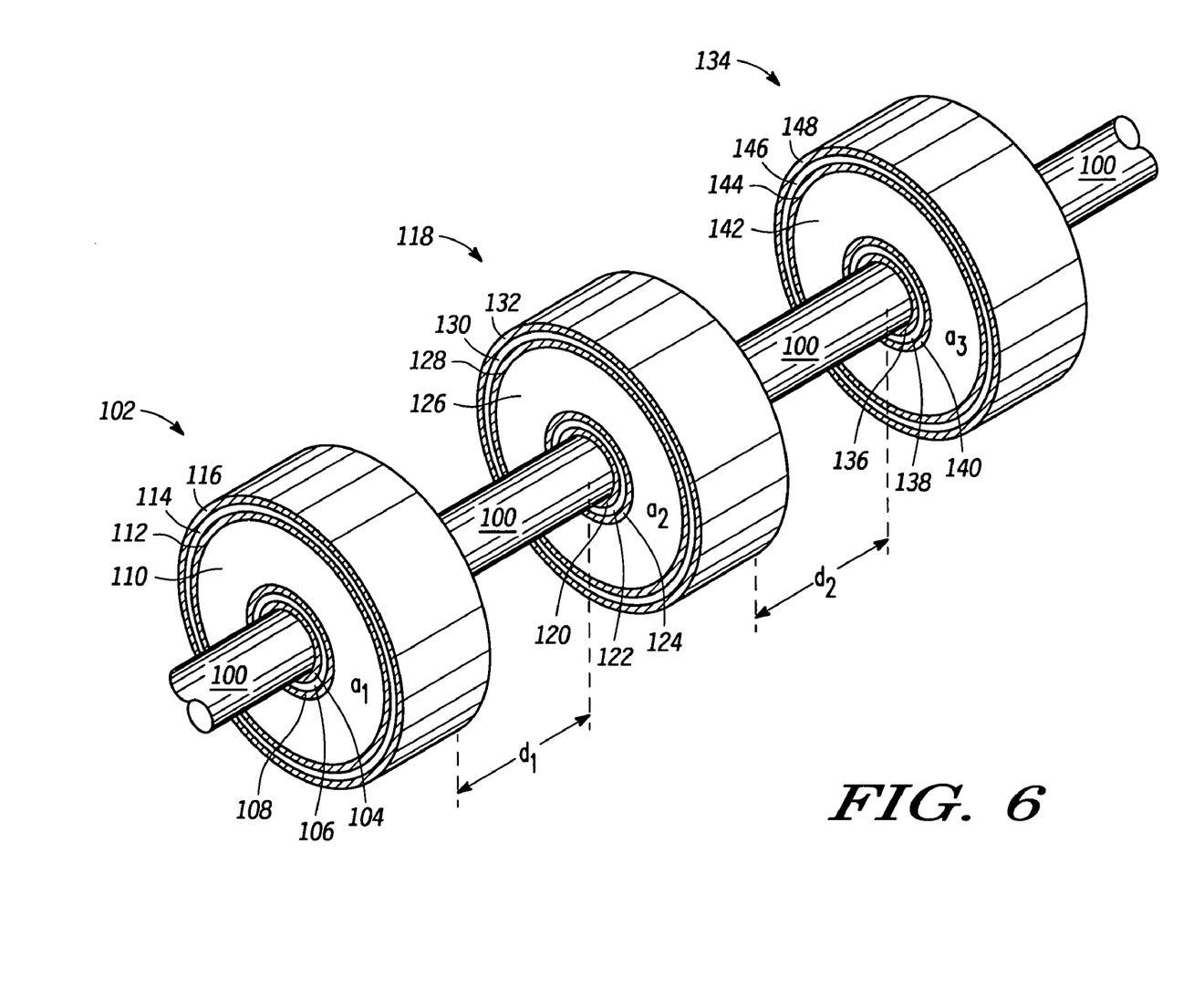
FIGS. 6-11 illustrates various embodiments of electrode configurations capable of use with the e-field system of FIG. 2.

FIG. 6 illustrates a member 100 which is subject to frozen material accumulation. For example, member 100 may be subject to frost formation. In one embodiment, member 100 is a cooling or evaporative element of a refrigerator or air conditioner. FIG. 6 illustrates three electrode assemblies 102, 118, and 134 which at least partially surround member 100. Note that in the illustrated embodiment, electrode assemblies 102, 118, and 134 each fully surround member 100. In one embodiment, member 100 is a grounded conductive member. Electrode assembly 102 includes an insulating layer 104 surrounding member 100, a conductive layer 106 surrounding insulating layer 104, an insulating layer 108 surrounding conductive layer 106, an electrode 110 surrounding insulating layer 108, an insulating layer 112 surrounding electrode 110, a conductive layer 114 surrounding insulating layer 112, and an insulating layer 116 surrounding conductive layer 114. Therefore, note that insulating layer 104, conductive layer 106, insulating layer 106, electrode 110, insulating layer 112, conductive layer 114, and insulating layer 116 form concentric rings.

Similarly, electrode assembly 118 includes an insulating layer 120 surrounding member 100, a conductive layer 122 surrounding insulating layer 120, an insulating layer 124 surrounding conductive layer 122, an electrode 126 surrounding insulating layer 124, an insulating layer 128 surrounding electrode 126, a conductive layer 130 surrounding insulating layer 128, and an insulating layer 132 surrounding conductive layer 130. Therefore, note that insulating layer 120, conductive layer 122, insulating layer 124, electrode 126, insulating layer 128, conductive layer 130, and insulating layer 132 form concentric rings.

Similarly, electrode assembly 134 includes an insulating layer 136 surrounding member 100, a conductive layer 138 surrounding insulating layer 136, an insulating layer 140 surrounding conductive layer 138, an electrode 142 surrounding insulating layer 140, an insulating layer 144 surrounding electrode 142, a conductive layer 146 surrounding insulating layer 144, and an insulating layer 148 surrounding conductive layer 146. Therefore, note that insulating layer 136, conductive layer 138, insulating layer 140, electrode 142, insulating layer 144, conductive layer 146, and insulating layer 148 form concentric rings.

In one embodiment, each of electrodes 110, 126 and 142 correspond to one of electrodes 16 and each is therefore coupled to one of electrode terminals 38 of e-field sensor 14. Note that gap 20 is therefore located between electrode 110 and electrode 126 and between electrode 126 and electrode 142. That is, the lateral areas of electrodes 110, 126, and 142, denoted by $A_1, A_2, A_3$, respectively, form a capacitive structure with the lateral areas of neighboring electrodes. Although only three electrode assemblies are illustrated, any number may be used along member 100, depending on the number of available electrode terminals of e-field sensor 14. Also, conductive layers 106, 114, 122, 130, 138, and 146 are all coupled to shield output 36. Also, the descriptions provided above with respect to insulating layers 54 and 58 also apply to insulating layers 108, 104, 112, 116, 120, 124, 128, 132, 136, 140, 144, and 148.

In operation, note that when electrode assembly 118 is selected, electrode 126 is coupled to the selected electrode terminal of e-field sensor 14 and electrodes 110 and 142 are grounded. In this manner, note that a first capacitive element is formed between lateral faces of electrodes 110 and 126 facing each other, spaced a distance $d_1$ apart. Also, a second capacitive element is formed between lateral faces of electrodes 126 and 142 facing each other, spaced a distance $d_2$ apart (where $d_2$ may be the same or different than $d_1$, and where $d_1$ and $d_2$ are fixed). Therefore, note that this is equivalent to two capacitive elements coupled in parallel, such that their capacitances are additive. In this example, e-field output 34 is primarily representative of the sum of the capacitances and is therefore representative of the amount of frost or frozen material between electrodes 102 and 118 and between electrodes 118 and 134. Furthermore, each electrode can be measured in a different time slot to detect accumulation of frozen material by selecting each electrode in turn. In this manner, by having multiple electrodes, a more reliable evaluation of frozen material accumulation may be made. Furthermore, in this embodiment, note that electrode 126 may correspond to one of electrodes 16 and electrodes 110 and 134 (the non-selected electrodes) may correspond to electrodes of electrodes 18 of FIG. 2.

In an alternate embodiment, if member 100 is electrically isolated from ground, insulating layers 108, 120, and 136, and conductive layers 106, 122, and 138 may not be present. In this case, insulating layers 104, 124, and 140 would be adjacent member 100. Also, in this embodiment, member 100 may be coupled to shield output 36.

Figure 7:
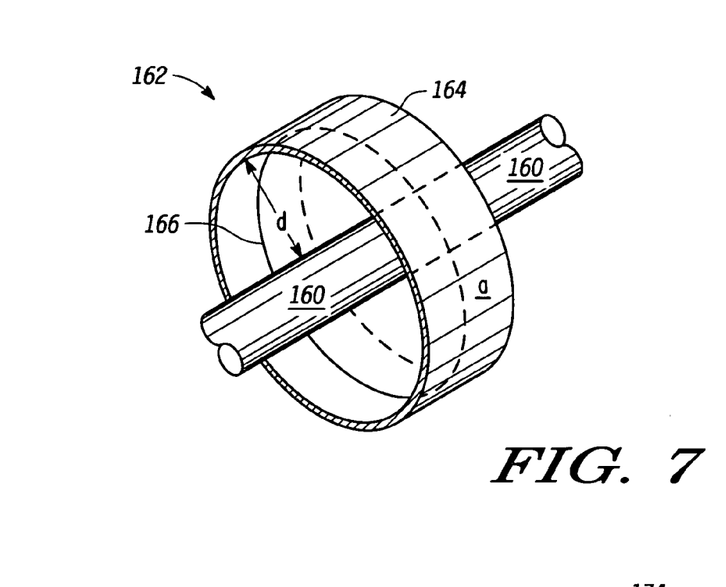
Figure 8:
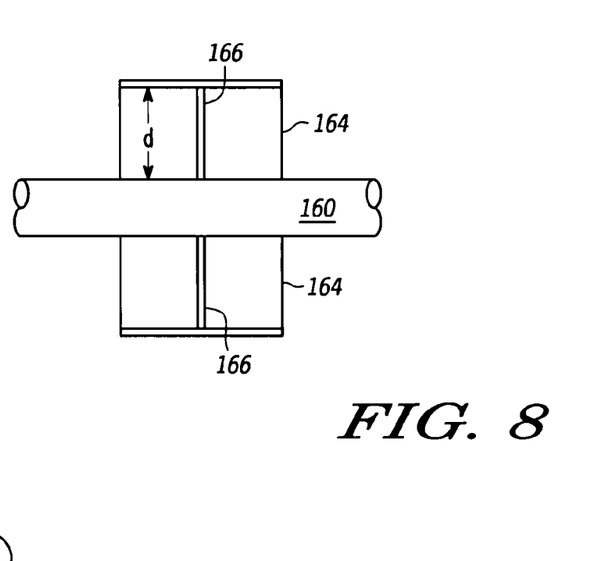

FIGS. 7 and 8 illustrate different views of a member 160 which is subject to frozen material accumulation. For example, member 160 may be subject to frost formation. In one embodiment, member 160 is a cooling or evaporative element of a refrigerator or air conditioner. FIGS. 7 and 8 illustrate an electrode assembly 162 which includes a conductive layer 164 which at least partially surrounds member 160. In the illustrated embodiment, conductive layer 164 fully surrounds member 160, and is spaced a distance d away from member 160. Note that in the illustrated embodiment, member 160 is positioned through the center of the ring formed by conductive layer 164, but alternatively, may not be through the center. In the illustrated embodiment, conductive layer 164 is held in position by a disk 166, which may be formed of a non-conductive material. Conductive layer 164 is coupled to one of electrode terminals 38 of e-field sensor 14 such that conductive layer 164 forms one of electrodes 16. In this embodiment, note that member 160 forms one of electrodes 18 where gap 20 is located between conductive layer 164 and member 160. Therefore, conductive layer 164 and member 160 form a capacitive element. In this embodiment, frozen material accumulation is detected along member 160 within the ring formed by conductive layer 164. Any number of rings may be present along member 160, and other physical support methods, other than disk 166, may be used to hold the ring or rings in place. Also, in one embodiment, member 160 is coupled to ground.

Figure 9:
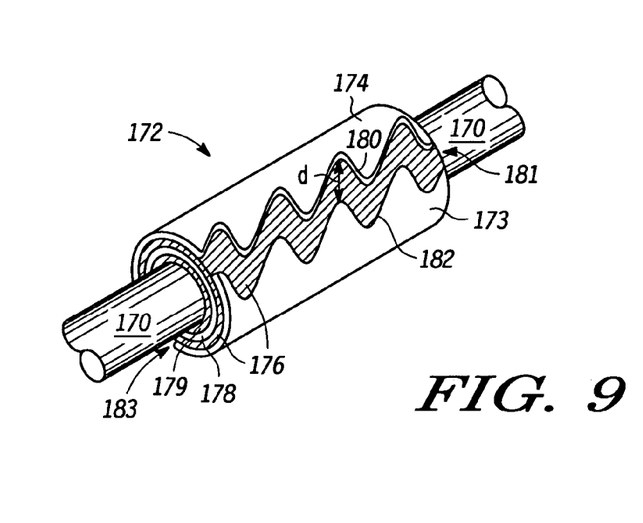

FIG. 9 illustrates a member 170 which is subject to frozen material accumulation. For example, member 170 may be subject to frost formation. In one embodiment, member 170 is a cooling or evaporative element of a refrigerator or air conditioner. FIG. 9 illustrates an electrode assembly 172 which surrounds member 170. Electrode assembly 172 includes an insulating layer 179 surrounding member 170, a conductive layer 178 surrounding insulating layer 179, and insulating layer 176 surrounding conductive layer 178, and conductive layers 173 and 174 partially surrounding insulating layer 176. Note that, in the illustrated embodiment, insulating layer 179 completely surrounds member 170, conductive layer 178 completely surrounds insulating layer 180, and insulating layer 176 complete surrounds conductive layer 178. However, conductive layers 174 and 173 do not completely surround insulating layer 176. Instead, they are spaced apart by a distance d. For example, in one embodiment, a gap 181 is formed along a lateral side of member 170 between edge 180 of conductive layer 174 and edge 182 of conductive layer 173, as is visible in FIG. 9. Also, in the illustrated embodiment, another similar gap 183 exists between conductive layers 174 and 173 along an opposite lateral side of member 170 (which is not fully visible in the view presented in FIG. 9). That is, the edges of conductive layers 174 and 173 opposite to edges 180 and 182, respectively, would also be spaced apart by a distance which may be the same or different than distance d between edges 180 and 182.

Note that the edges of conductive layers 174 and 173, such as edges 180 and 182, can have any shape, so long as a gap is present between the edges, as is visible along the front of member 170 in FIG. 9. In this embodiment, conductive layer 178 is coupled to shield output 36 of e-field sensor 14, conductive layer 174 is coupled to one of electrode terminals 38 of e-field sensor 14, and conductive layer 173 is coupled to another one of electrode terminals 38 of e-field sensor 14. In this embodiment, one of conductive layers 174 and 173 can be considered one of electrodes 16, while the other of conductive layers 174 and 173 can be considered one of electrodes 18. Therefore, note that conductive layers 174 and 173 form a capacitive element. In this manner, gap 20 corresponds to gap 181 between edges 180 and 182 (and gap 183 between the edges opposite edges 180 and 182) along lateral sides of member 170, such that e-field output 34 is representative of an amount of frozen materials located between the edges of conductive layer 174 and the edges of conductive layer 173.

In one embodiment, each of conductive layers 174 and 173 can be approximately the same size, such that the gaps between their edges are located exactly opposite each other on either side of member 170. In alternate embodiments, conductive layers 174 and 173 may not be the same size, and the gaps between their edges can be located anywhere around member 170. Also, in alternate embodiments, any number of conductive layers such as conductive layers 173 and 174 may be used to surround member 170, where they may be coupled to additional electrode terminals of electrode terminals 38. For example, in the case of 3 conductive layers where each conductive layer is coupled to one terminal of electrode terminals 38 of e-field sensor 14, one can be selected while the other two are coupled to ground where the equivalence of two capacitive elements in parallel are formed, similar to the configuration described above in reference to FIG. 6. Also, these conductive layers may be of any size, or can all be of equal size.

Also, note that if member 170 is electrically isolated from ground, conductive layer 178, and one of insulating layers 179 and 176 need not be present. Also, in this embodiment, member 170 may be coupled to shield output 36.

Figure 10:
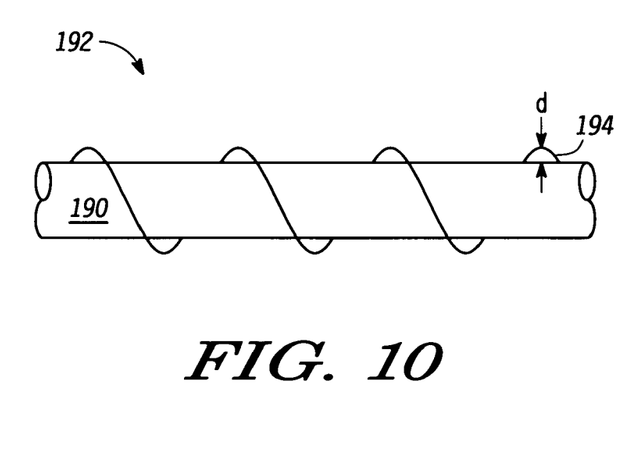

FIG. 10 illustrates a member 190 which is subject to frozen material accumulation. For example, member 190 may be subject to frost formation. In one embodiment, member 190 is a cooling or evaporative element of a refrigerator or air conditioner. FIG. 10 illustrates an electrode assembly 192 which includes an insulated wire 194 which is wrapped around member 190 and spaced a distance d apart from member 190. In this embodiment, wire 194 can be considered one of electrodes 16 and is coupled to one of electrode terminals 38 of e-field sensor 14, and member 190 itself may be considered one of electrodes 18. In this manner, e-field output 34 is representative of the amount of frozen material located between wire 194 and member 190 along member 190 where wire 194 and member 190 form a capacitive element. Also, in this case, note that the area of the capacitor electrode formed by wire 194 is approximately the diameter of the wire integrated over the length of member 190. In this embodiment, member 190 may be coupled to ground.

Figure 11:
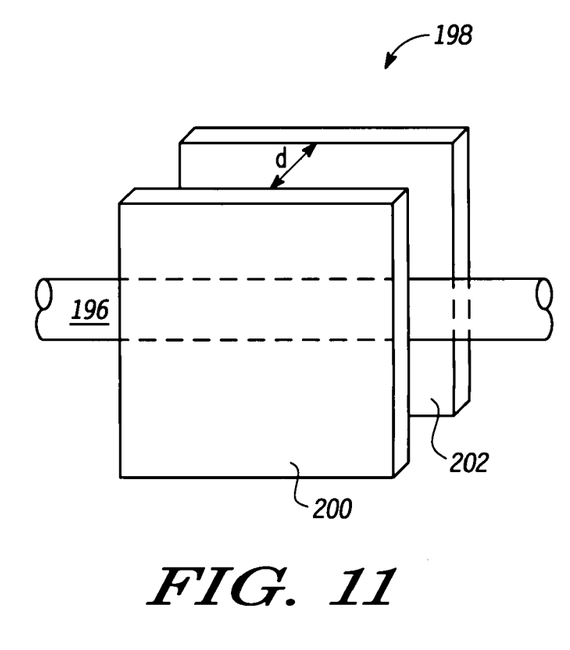

FIG. 11 illustrates a member 196 which is subject to frozen material accumulation. For example, member 196 may be subject to frost formation. In one embodiment, member 196 is a cooling or evaporative element of a refrigerator or air conditioner. FIG. 11 illustrates an electrode assembly 198 which includes two conductive plates 200 and 202 spaced apart by a distance d, where member 196 is located between plates 200 and 202. In one embodiment, each of plates 200 and 202 is coupled to an electrode terminal of e-field sensor 14. If member 196 is grounded, then e-field output 34 is representative of an amount of frozen material located between one of plates 200 and 202 (a selected plate) and member 196. If member 196 is electrically isolated from ground, then e-field output 34 may be representative of an amount of frozen material located between plates 200 and 202. That is, in this example, one of plates 200 and 202 can be selected as the selected electrode where the other one of plates 200 and 202 is coupled to ground.

Figure 12:
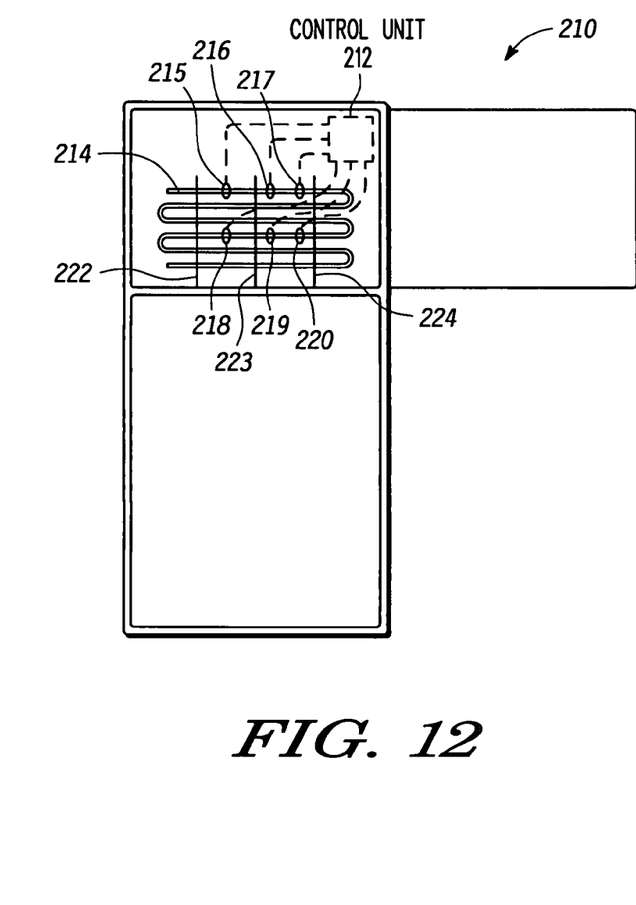
FIGS. 12-13 illustrate various applications for the e-field system of FIG. 2, in accordance with various embodiments of the present invention.

Therefore, it can be appreciated that many different forms of electrodes 16 and 18 may be used to define gap 20 (and thus define a capacitive element) such that an accumulation of frost or other frozen material may be detected. As stated above, the electrodes can be used to detect accumulation of frozen material in a refrigerator or air conditioner. Therefore, FIG. 12 illustrates a cooling device 210 which can be any type of cooling device such as, for example, a refrigerator or air conditioner, which includes a cooling element 214 that may be held in place by support elements 224. Any number of electrodes, such as electrodes 215-220 may be used along cooling element 214 and coupled to a control unit 212 included somewhere within or external to cooling device 210. E-field sensor 14 and processor 12 can be included, for example, in control unit 212, and electrodes 215-220 may be implemented in any of the configurations described above or in any other configuration. Therefore, although a refrigerator is illustrated where electrodes 215-220 may be used in a colder compartment of the refrigerator, such as a freezer, cooling device 210 may be any type of cooling device, where cooling element 214 and electrodes 215-220 may be used anywhere within cooling device 210.

Figure 13:
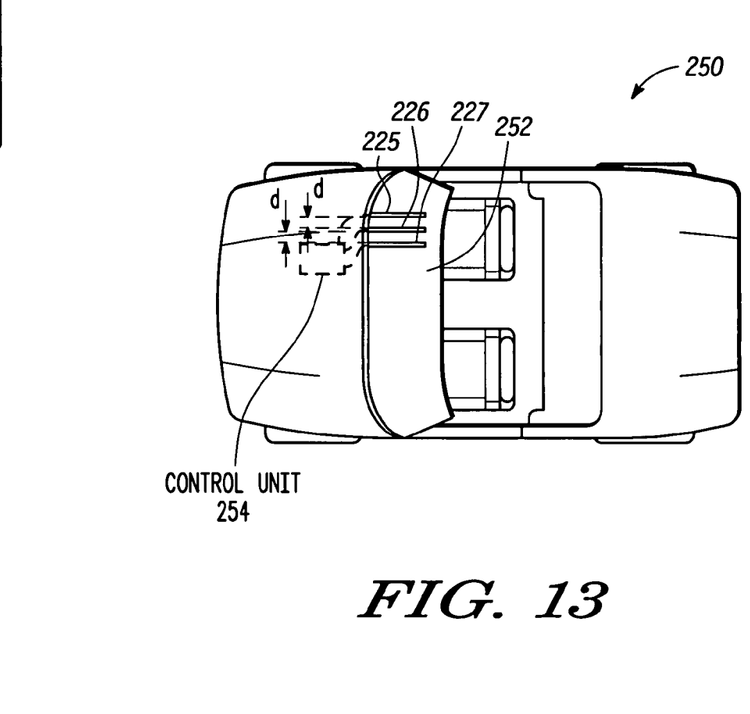

FIG. 13 illustrates an example of a transportation device 250 which includes a member 252 that is subject to frozen material accumulation. Member 252 may be a windshield or other window. Similarly, it can be any other part of transportation device 250 (e.g. a door, wing, etc.) that is subject to frozen material accumulation. Also, transportation device 250 can be any type of transportation device such as an automobile, air craft, or other vehicle. In the illustrated embodiment, a plurality of electrodes 225-227 are formed within windshield 252. For example, they can be formed using a clear conductive material, such as, for example, indium titanium oxide. Each of these can be coupled to an electrode terminal of an e-field sensor (such as e-field sensor 14) located within control unit 254 that may be located anywhere within transportation device 250. In this manner, frozen material can be detected between adjacent electrodes, in a manner similar to that described in reference to FIG. 6 which illustrates a plurality of electrodes located along member 100. That is, for example, when an electrode terminal coupled to sensor 226 is selected, other electrode terminals coupled to sensors 225 and 227 may be grounded. In this manner, an e-field output of the e-field sensor outputs a value that is primarily representative of frozen material accumulation between sensors 225 and 227 since, when sensor 226 is selected, sensors 225-227 form two capacitive elements coupled in parallel.

Windshield 252 may include any number of electrodes such as electrodes 225-227, where each electrode can be selected in turn such that e-field output may be primarily representative of frozen material accumulation between adjacent electrodes of the selected electrode (where the selected electrode is located between the adjacent electrodes). Also, in one embodiment, the adjacent electrodes refer to those electrodes which are immediately adjacent the selected electrode. Also, note that when an edge electrode is selected, such as electrode 225, the e-field output would be primarily representative of the frozen material accumulation between electrode 225 and 226, a single capacitive element. Note that, as with the embodiment of FIG. 6, adjacent electrodes which are not immediately adjacent to the selected electrode may also affect capacitance and thus the e-field output. However, the effect of these further away electrodes does not greatly affect the output, thus e-field output is primarily representative of the capacitive elements formed with immediately adjacent electrodes of the selected electrode, as has been described above.

In alternate embodiments, electrodes, such as electrodes 225-227, may be located anywhere on transportation device 250, as needed. For example, electrodes coupled to an e-field sensor may be located on a door of a car or airplane or on a wing of an airplane. Furthermore, different e-field sensors and corresponding electrodes may be located in various different locations to detect frost accumulation in more than one location of the transportation device.

Therefore, it can be appreciated how system 10 can be used in a variety of different ways to detect accumulation of frozen material and to determine when a particular action or actions should be taken to clear or reduce the accumulation of frozen material, based on the values of e-field output 34. In this manner, these actions may be performed on an as-needed basis, thus improving efficiency and reducing operating costs. Furthermore, electrodes 16 and 18 and gap 20 can be configured in many different ways, and shield output 36 can be used, as needed, to shield electrode 16 from being over powered by neighboring conductive elements.

Note that the conductors as discussed herein in reference to FIG. 2 may be illustrated or described in reference to being a single conductor, a plurality of conductors, unidirectional conductors, or bidirectional conductors. However, different embodiments may vary the implementation of the conductors. For example, separate unidirectional conductors may be used rather than bidirectional conductors and vice versa. Also, plurality of conductors may be replaced with a single conductor that transfers multiple signals serially or in a time multiplexed manner. Likewise, single conductors carrying multiple signals may be separated out into various different conductors carrying subsets of these signals. Therefore, many options exist for transferring signals.

In the foregoing specification, the invention has been described with reference to specific embodiments. However, one of ordinary skill in the art appreciates that various modifications and changes can be made without departing from the scope of the present invention as set forth in the claims below. For example, software may be used within processor 12 to perform the all or parts of the flow of FIG. 5. Any software may be embodied on one or more of computer hard disks, floppy disks, 3.5" disks, computer storage tapes, magnetic drums, static random access memory (SRAM) cells, dynamic random access memory (DRAM) cells, electrically erasable (EEPROM, EPROM, flash) cells, nonvolatile cells, ferroelectric or ferromagnetic memory, compact disks (CDs), laser disks, optical disks, and any like computer readable media. Also, the block diagrams may include different blocks than those illustrated and may have more or less blocks or be arranged differently. Also, the flow diagrams may also be arranged differently, include more or less steps, or may have steps that can be separated into multiple steps or steps that can be performed simultaneously with one another. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. An apparatus comprising:
   a first electrode;
   a second electrode located at a distance from the first electrode, the second electrode forming a capacitive element with the first electrode, wherein a gap is present between the first and second electrodes, wherein each of the first electrode and second electrode partially surrounds a member subject to accumulation of frozen material, such that the gap is formed between edges of the first and second electrodes along lateral sides of the member;
   an electric field sensor having an electrode terminal coupled to the first electrode and providing an electric field output value representative of an amount of frozen material located in the gap between the first and second electrodes;
   a first insulating layer around the member, between the member and the first electrode and between the member and the second electrode; and
   a conductive layer around the member, between the member and the first insulator, wherein a shield output of the electric field sensor is coupled to the conductive layer.

2. The apparatus of claim 1, further comprising:
   a coaxial cable, wherein the electrode terminal is coupled to the first electrode via a center conductor of the coaxial cable and wherein a shield output of the electric field sensor is coupled to the conductive layer via an outer shield of the coaxial cable.

3. The apparatus of claim 2, wherein the shield output maintains an approximately zero voltage differential between the center conductor and the outer shield.

4. The apparatus of claim 1, wherein the second electrode is subject to frost accumulation and the first electrode at least partially surrounds the second electrode 5. The apparatus of claim 1, wherein the member is at least a portion of a cooling element.

6. The apparatus of claim 1, further comprising a refrigerator or air conditioner, the refrigerator or air conditioner comprising the first electrode, the second electrode, the electric field sensor, the first insulating layer, and the first conductive layer.

7. The apparatus of claim 1, further comprising a transportation device, the transportation device comprising the first electrode, the second electrode, the electric field sensor, the first insulating layer, and the first conductive layer.

8. The apparatus of claim 7, wherein the transportation device comprises a window, the window comprising the first and second electrodes.

9. The apparatus of claim 8, wherein the first and second electrodes each comprises indium titanium oxide.

10. The apparatus of claim 7, wherein the transportation device comprises a wing, the wing comprising the first and second electrodes.

11. An apparatus comprising:
    a member subject to accumulation of frozen material;
    a first electrode at least partially surrounding the member;

a second electrode at least partially surrounding the member and located at a first distance from the first electrode, the second electrode forming a capacitive element with the first electrode;

an electric field sensor having a first electrode terminal coupled to the first electrode and providing an electric field output value representative of an amount of frozen material formed on the member between the first and second electrodes; and a third electrode at least partially surrounding the member and located at a second distance from the first electrode, the first electrode between the second and third electrodes;

wherein the electric field sensor comprises a second electrode terminal coupled to the second electrode and a third electrode terminal coupled to the third electrode, and wherein when the first electrode terminal is enabled, the electric field output value is representative of an amount of frozen material formed on the member between the second and third electrodes.

12. The apparatus of claim 11, wherein when the first electrode terminal is enabled, the second electrode terminal couples the second electrode to ground and the third electrode terminal couples the third electrode to ground.

13. The apparatus of claim 11, further comprising:

a first insulating layer at least partially surrounding the first electrode;

a first conductive layer at least partially surrounding the first insulating layer, wherein a shield output of the electric field sensor is coupled to the first conductive layer;

second insulating layer at least partially surrounding the second electrode; and a second conductive layer at least partially surrounding the second insulating layer, wherein the shield output of the electric field sensor is coupled to the second conductive layer.

14. The apparatus of claim 13, wherein the first electrode, first insulating layer, and first conductive layer form concentric rings, and wherein the second electrode, second insulating layer, and second conductive layer form concentric rings.

15. The apparatus of claim 11, wherein the member subject to frozen material accumulation comprises a cooling element of a refrigerator or air conditioner.

16. An apparatus comprising:

a member subject to accumulation of frozen material;

a first electrode at least partially surrounding the member;

a second electrode at least partially surrounding the member and located at a first distance from the first electrode, the second electrode forming a capacitive element with the first electrode;

an electric field sensor having a first electrode terminal coupled to the first electrode and providing an electric field output value representative of an amount of frozen material formed on the member between the first and second electrodes;

a first insulating layer at least partially surrounding the first electrode;

a first conductive layer at least partially surrounding the first insulating layer, wherein a shield output of the electric field sensor is coupled to the first conductive layer;

a second insulating layer at least partially surrounding the second electrode; and a second conductive layer at least partially surrounding the second insulating layer, wherein the shield output of the electric field sensor is coupled to the second conductive layer;

a third insulating layer at least partially surrounding the member, the third insulating layer between the member and the first electrode;

a third conductive layer at least partially surrounding the member, the third conductive layer between the member and the third insulating layer, wherein the shield output of the electric field sensor is coupled to the third conductive layer;

a fourth insulating layer at least partially surrounding the member, the fourth insulating layer between the member and the third conductive layer;

a fifth insulating layer at least partially surrounding the member, the fifth insulating layer between the member and the second electrode;

a fourth conductive layer at least partially surrounding the member, the fourth conductive layer between the member and the fifth insulating layer, wherein the shield output of the electric field sensor is coupled to the fourth conductive layer; and a sixth insulating layer at least partially surrounding the member, the sixth insulating layer between the member and the fourth conductive layer.

17. The apparatus of claim 16, wherein the first electrode, first insulating layer, and first conductive layer form concentric rings, and wherein the second electrode, second insulating layer, and second conductive layer form concentric rings.

18. The apparatus of claim 16, wherein the member subject to frozen material accumulation comprises a cooling element of a refrigerator or air conditioner.

* * * * *